US010551285B2

(12) United States Patent
Gaechter et al.

(10) Patent No.: US 10,551,285 B2
(45) Date of Patent: Feb. 4, 2020

(54) SAMPLE TRANSFER DEVICE

(71) Applicant: Leica Mikrosysteme GmbH, Vienna (AT)

(72) Inventors: Leander Gaechter, Oberriet (CH); Günther Bock, Vienna (AT); Thomas Pfeifer, Zschopau (DE)

(73) Assignee: Leica Mikrosysteme GmbH, Vienna (AT)

( * ) Notice: Subject to any disclaimer, the term of this patent is extended or adjusted under 35 U.S.C. 154(b) by 214 days.

(21) Appl. No.: 15/543,326

(22) PCT Filed: Jan. 14, 2016

(86) PCT No.: PCT/EP2016/050606
§ 371 (c)(1),
(2) Date: Jul. 13, 2017

(87) PCT Pub. No.: WO2016/116341
PCT Pub. Date: Jul. 28, 2016

(65) Prior Publication Data
US 2017/0370814 A1    Dec. 28, 2017

(30) Foreign Application Priority Data

Jan. 20, 2015   (DE) .................. 10 2015 100 727

(51) Int. Cl.
*G01N 1/42*       (2006.01)
*G01K 13/00*      (2006.01)
*G01L 19/00*      (2006.01)

(52) U.S. Cl.
CPC ............ *G01N 1/42* (2013.01); *G01K 13/006* (2013.01); *G01L 19/00* (2013.01)

(58) Field of Classification Search
USPC .......................................... 73/863
See application file for complete search history.

(56) References Cited

U.S. PATENT DOCUMENTS

| 4,637,226 | A | 1/1987 | Sitte |
| 7,644,637 | B2 * | 1/2010 | Moore ............... B25J 21/02 73/863 |
| 9,324,964 | B2 * | 4/2016 | Yamada ............. H01L 51/5215 |

(Continued)

FOREIGN PATENT DOCUMENTS

| DE | 4114427 A1 | 11/1992 |
| JP | S55153755 U | 11/1980 |
| JP | 2013257148 A | 12/2013 |

OTHER PUBLICATIONS

Leica EM VCT100: Vacuum Cryo Transfer, From Preparation to Analysis, May 2009, pp. 1-12.

(Continued)

*Primary Examiner* — Clayton E. LaBalle
*Assistant Examiner* — Warren K Fenwick
(74) *Attorney, Agent, or Firm* — Hodgson Russ LLP (57) ABSTRACT

The invention relates to a sample transfer device (10) for reception of a sample, having a transfer rod (4) that is configured for reception of a sample holder, the sample holder to be arranged in a chamber (1) of the sample transfer device (10) for the purpose of transferring the sample to a processing unit or analytical unit (200), at least one measurement device (3, 8) for measuring a physical variable being arranged inside the sample transfer device (10).

18 Claims, 4 Drawing Sheets

(56) References Cited

U.S. PATENT DOCUMENTS

| | | | |
|---|---|---|---|
| 9,494,551 B2* | 11/2016 | Gover | B01L 3/5027 |
| 2005/0214928 A1* | 9/2005 | Larsen | B01F 13/0059 |
| | | | 435/287.1 |
| 2006/0192116 A1* | 8/2006 | Baur | G01N 1/28 |
| | | | 250/310 |
| 2008/0217246 A1* | 9/2008 | Benn | G01N 35/00029 |
| | | | 210/645 |
| 2009/0078060 A1 | 3/2009 | Moore et al. | |

OTHER PUBLICATIONS

Chyongere Hsieh et al., Practical workflow for cryo focused-ion-beam milling of tissues and cells for cryo-TEM tomography, Journal of Structural Biology, 2014, vol. 185, pp. 32-41.

* cited by examiner

SAMPLE TRANSFER DEVICE

CROSS-REFERENCE TO RELATED APPLICATIONS

The present application is the U.S. national phase of International Application No. PCT/EP2016/050606 filed Jan. 14, 2016, which claims priority of German Application No. 10 2015 100 727.4 filed Jan. 20, 2015, the entire disclosure of which is incorporated herein by reference.

FIELD OF THE INVENTION

The invention relates to a sample transfer device for reception of a sample, in particular of a sample to be processed and/or to be investigated microscopically, having a transfer rod that is configured for reception of a sample holder, the sample holder to be arranged in a chamber of the sample transfer device for the purpose of transferring the sample to a processing unit or analytical unit.

BACKGROUND OF THE INVENTION

Sample transfer devices of this kind are utilized in particular in electron microscopy. Samples to be investigated, which contain e.g. cells, enzymes, viruses, or lipid layers, are cryofixed, i.e. the water-containing sample is frozen very quickly to temperatures below −150° C., avoiding the formation of ice crystals. The biological structures can thereby be kept in their natural state. For example, a biological process can be halted at any desired point in time by cryofixation and can be investigated, for example, in a cryo-electron microscope and/or in a light microscope with corresponding sample cooling. Prior to the actual investigation, cryofixed samples can be subjected to further preparation steps in a manner known per se, for example processing using freeze-fracturing, freeze-etching, and/or coating techniques.

In order not to impair the quality of the frozen samples, it is very important that they be transferred in contamination-free, and optionally cooled, fashion between the processing devices or analytical devices that are being used. "Processing devices" or "processing units" may be understood, for example, as a cryofixation device, a freeze-fracture apparatus, a freeze-etching apparatus, or a coating apparatus, while "analytical devices" or "analytical units" are to be understood, for example, as a cryo-electron microscope or a cooled light microscope.

So-called sample transfer devices are used for the purpose of conveying or transferring a sample to a processing unit or analytical unit. One such sample transfer device is represented, for example, by the "Leica EM VCT100" vacuum cryotransfer system (manufacturer: Leica Microsystems), which is described in the brochure of the same name that is accessible via the link: http://www.leica-microsystems.com/fileadmin/downloads/Leica%20EM%20VCT100/Brochures/Leica_EM VCT100_Brochure_EN.pdf. This transfer system comprises a transfer rod for detachable mounting of a sample holder, the latter being arranged at the end of the transfer rod. If a very small frozen electron microscopy sample is present on the sample holder, the latter can be picked up by suitable displacement of the transfer rod and by connection to the sample holder, the sample then being arranged, by another (backward) displacement of the transfer rod, in a chamber of the transfer system for the purpose of transferring the sample to a processing unit or analytical unit. In the chamber, the sample is kept under inert gas or under high vacuum and, to the extent necessary, at the low temperature necessary for further cryo-processing or cryo-investigation. The transfer system attachment system is configured in such a way that a high-vacuum connection to the processing unit or analytical unit can thereby be created. The chamber or the sample holder is furthermore in communication with a coolant reservoir, usually a Dewar container, that can be filled with a coolant, typically liquid nitrogen. The sample holder, and the sample present thereon, are thereby cooled.

A plurality of different sample holders are available depending on the particular processing unit or analytical unit, and are depicted in the aforesaid brochure. After cryofixation of the sample, the latter is loaded into the vacuum transfer system with a suitable sample holder. Transfer to the downstream processing unit or analysis unit then occurs. The transfer is accomplished in a cooled state, so that the sample cannot incipiently or completely thaw and thus become unusable. Contamination, for example upon exposure of the sample to ambient air, is also to be avoided. Sample transfer devices, such as the above-described "Leica EM VCT100" vacuum cryotransfer system, comprise vacuum sliders or slide valves so that the sample can be introduced, for example under vacuum, into the corresponding processing device or analytical device. For example, a slide valve is arranged at the attachment point of the sample transfer device, and a further slide valve at the corresponding attachment point of the processing unit or analytical unit. After attachment of the sample transfer device to the processing unit or analytical unit with the respective slide valves closed, the cavity that is produced is evacuated in the manner of an air lock. The slide valves are then opened, and the sample is then transferred under vacuum to the processing unit or analytical unit. For this, the transfer rod can be displaced linearly and often also rotated around its axis.

It has been found that changes in the state of the sample during transfer can lead to damage to the sample, and thus misinterpretations or unusable results upon analysis, or can complicate subsequent processing steps or make them entirely impossible. Sample transfer is often accomplished in time-controlled fashion based on empirical values.

SUMMARY AND ADVANTAGES OF THE INVENTION

The object of the present invention is therefore to further decrease the probability of a sample-damaging change of state, and to detect such a change of state without a long delay.

To achieve this object, a sample transfer device according to the present invention is proposed. Advantageous embodiments are evident from the description below.

A sample transfer device according to the present invention comprises a chamber in which a sample holder can be arranged. An inert gas atmosphere, or a vacuum (high vacuum) usually exists in this chamber. Cryogenic temperatures usually exist in the chamber. According to the present invention, at least one measurement device for measuring a physical variable is arranged inside the sample transfer device.

The invention makes it possible to measure, and optionally also to monitor, physical variables, in particular those that influence a sample present in the chamber.

Physical variables that can be recited are, in particular, the temperature and the pressure in the chamber of the sample transfer device. Other variables are also conceivable, however, such as the chamber volume, the number of particles in the atmosphere of the chamber, the location and orientation of a sample that is located on a sample holder that in turn is connected to the transfer rod of the sample transfer device. Measurement of the physical variable of time, for example the duration of a transfer of the sample to a processing unit or analytical unit or between processing units and/or analytical units, also represents an important variable.

What is meant by a "measurement device" in the context of this Application is firstly only the sensor or probe that measures the relevant physical variable so that a corresponding signal (usually a voltage signal or current signal) is generated. It is only in a further sense, which is likewise intended to be encompassed, that a "measurement device" also means a circuit or electronic system that encompasses the aforesaid sensor or probe and generates a signal that can already be conditioned for subsequent further processing.

It is advantageous if a measurement device for measuring a pressure existing in the chamber is present in the interior of the sample transfer device. Pressure measurement devices are known per se; they encompass, for example, piezoresistive or piezoelectric pressure sensors, capacitive or inductive pressure sensors, etc. Suitable pressure sensors correspondingly exist in the vacuum sector, for example a thermal conductivity vacuum gauge or an ionization vacuum gauge.

It is furthermore advantageous if a measurement device for measuring a temperature existing in the chamber of the sample transfer device is present. The transfer rod is equipped with a corresponding gripper for reception of a sample holder. Via the transfer rod, the sample holder having the sample arranged thereon is transferred to or from a sample stage arranged in the chamber. The temperature measurement device can be connected, for example, to one of the aforesaid elements, preferably to the sample stage, if that element is thermally conductively connected to the sample holder and to the sample present thereon. For purposes of this Application, the arrangement of a measurement device on an element of this kind connected to the transfer rod of the sample transfer device is to be encompassed by an "arrangement inside the sample transfer device." It is advantageous to measure the temperature of the sample stage by means of a temperature sensor that is arranged on the sample stage. The sample temperature can thereby be determined to a good approximation, since the sample stage and the sample holder having the sample are thermally conductively connected to one another. Temperature sensors are known per se. To be recited here are, in particular, NTC and PTC thermistors, whose resistance depends on temperature and which can therefore be used for temperature measurement. On the other hand there exist integrated semiconductor temperature sensors that supply a proportional current, a proportional voltage, or in general a temperature-dependent signal as a function of temperature. Other temperature sensors are also known.

Because previously known sample transfer devices do not possess their own system for measuring physical variables influencing the state of a sample, it was hitherto not possible to measure, for example, the sample temperature and the pressure after closure of the chamber of the sample transfer device. Only after the sample had been transferred into a subsequent processing unit or analytical unit could the sample again be brought into a defined state. A measurement of, for example, the sample temperature and the pressure could only be made in the corresponding processing device or analytical device. The history of the sample state during the transfer was unknown. With the present invention it is now possible to determine the state of the sample, based on the physical variables determining the sample state, by means of the at least one measurement device inside the sample transfer device.

The measurement of the at least one physical variable can be made before the actual transfer, during the transfer, and/or after the actual transfer. This also depends on whether the measurement devices present in the sample transfer device themselves have a supply of electricity. Be it noted that an independent supply of electricity is not obligatorily necessary. As a rule, the transfer occurs from a loading station to a processing unit, between two processing units, or between a processing unit and an analytical unit, or also between two analytical units, the aforesaid units each possessing a docking station onto which a sample transfer device can be attached. It is possible in principle to implement a supply of electricity to the at least one measurement device inside the sample transfer device via a docking station of this kind, and correspondingly also to perform the measurement and the transfer of measured values into the docking station only after docking, whereupon further processing of the measured values occurs.

In such a case the aforesaid physical variables, such as temperature and pressure, would be measured at the respective docking stations. In the uncoupled state, i.e. during a transfer, the electrical supply to the at least one measurement device would then be interrupted. The measured values absent during the transfer can then usefully be interpolated.

A sufficiently accurate description of the history of the sample state is thereby obtained respectively by way of measured values upon docking onto the aforesaid units (loading, processing, and analytical units), and during transfer (by interpolation). This allows identification of sample-damaging changes of state, which can be detected in particular immediately after docking onto one of the aforesaid units. Unusable results or misinterpretations upon subsequent analysis can thus be avoided, or sample states that are unsuitable for further processing can also be detected a priori.

It is furthermore advantageous if a time measurement device is present inside the sample transfer device. A time measurement device of this kind can, for example, be activated upon removal of the sample transfer device from a docking station and deactivated upon re-docking onto a docking station, so that what is measured as a measured variable is the transfer time. This transfer time can be conveyed and processed, for example, via the docking station of the respective unit. If this transfer time is, for example, greater than a permissible limit value, this can be an indication of a sample-damaging change of state. Alternatively or additionally (for verification) the history of further physical variables, such as temperature and pressure, can be employed in order to identify any sample damage.

Instead of an interpolation of measured values, it can also be useful and appropriate to measure the respective physical variables continuously, or at least at specific time intervals, during a transfer. A rechargeable battery, in particular, is arranged for this purpose, for example, inside the sample transfer device in order to supply electricity to the at least one measurement device. Other energy suppliers, such as primary batteries or a wireless energy transfer (inductive, capacitive delivery) are also conceivable and possible. A rechargeable battery has the advantage that it can be charged in simple fashion, for example via the docking station upon docking of the sample transfer device. When the rechargeable battery is arranged inside the sample transfer device, attention must be paid to adequate temperature- and/or pressure-insulated encapsulation. In order to avoid this, the rechargeable battery (or other energy supplier) can also be arranged outside, for example on the housing of, the sample transfer device, and can be connected to the at least one measurement device in the interior of the sample transfer device, for example, via corresponding pressure- and/or temperature-resistant connectors.

It is particularly advantageous if an electronic control system is present, which is operatively connected to the at least one measurement device in such a way that a measurement can be initiated by the relevant measurement device and/or measured values of the relevant measurement device can be received by the electronic control system. The necessary measurement processes, control processes, and other regulation processes can thereby be implemented via an integrated electronic control system. Like the rechargeable battery, the electronic control system can be arranged inside or outside the sample transfer device. The same statements as for the rechargeable battery thus apply here.

As already mentioned, sample transfer devices usually possess an attachment point to the respective docking stations of subsequent processing devices or analytical devices. It is advantageous if the corresponding attachment system of the sample transfer device comprises an interface by way of which the measured values of the at least one measurement device are transferred to the attached processing unit or analytical unit or to a docking station in communication therewith. It is furthermore advantageous if the at least one measurement device is supplied with electricity by way of this interface as soon as the sample transfer device is docked onto the relevant processing unit or analytical unit. The transferring of the measured values on the one hand, and the supplying of electricity on the other hand, can be effected and controlled in particular via an electronic control system that is present. Lastly, the electronic control system itself can also be exclusively or additionally supplied with electricity via the aforementioned interface.

If a rechargeable battery is present in or on the sample transfer device, it is advantageous to charge it via the interface by means of an external current source.

As explained, sample transfer devices comprise a transfer rod at the end of which a sample holder is detachably mounted. The location of the sample holder, and thus also of the sample, can be modified by linear motion of the transfer rod. The orientation of the sample holder, and thus of the sample, can often also be modified by rotating the transfer rod around its axis. The sample transfer device can also comprise, for the purpose of receiving a sample holder, a sample stage that is located at the end of the transfer rod. It is advantageous in this connection if the location of the sample stage or of the sample holder, and/or a corresponding motion (x) of the transfer rod, is detected, and/or if a corresponding rotation ($\alpha$) of the transfer rod is detected, by means of a further measurement device. It can furthermore be useful to measure the location and orientation of the sample in three dimensions, or to derive them from measured values of the aforesaid measurement device. A history of the sample position during a transfer, or at least before and after a transfer, can thereby be created. The aforesaid measurement device can represent a location sensor and/or motion sensor that is arranged in the interior of the sample transfer device, in particular in the interior of the chamber thereof. Alternatively, it can be useful to measure a motion (x) and/or a rotation (a) by way of corresponding (known) sensors on the transfer rod outside the sample transfer device.

It can be advantageous if the aforesaid electronic control system generates a warning signal if a measured value of the at least one measurement device exceeds or falls below a predetermined limit value. For example, if the pressure in a vacuum chamber exceeds a maximum permissible limit value, a corresponding warning signal is generated and can be immediately transferred outward (for example, via radio) or can be transferred and displayed (acoustic and/or optical display) immediately upon docking of the sample transfer device onto a docking station. The same applies analogously, for example, to the measured value for the temperature, in particular for cryofixed samples. The same applies in turn to the measured value, explained above, for the duration of a transfer, which should be, for example, below a predefined limit value.

The invention further relates to a system having a sample transfer device according to the present invention that comprises an interface to a docking station of a processing unit or analytical unit, and having such a docking station. It is advantageous in this context if the interface of the sample transfer device possesses a contact, in particular an electrical contact, further in particular a resilient electrical contact, and if the docking station possesses a corresponding contact, in particular an electrical contact, in particular likewise a resilient electrical contact, those contacts being arranged and configured in such a way that upon a connection of the sample transfer device and the docking station, the aforesaid contacts enter into an operative connection with one another. It is then possible thereby, in particular, for the aforesaid measured values to be transferred to the docking station and/or to the associated processing unit or analytical unit. On the other hand, the at least one measurement device and/or electronic control system of the sample transfer device can be supplied with electricity via the mutually connected contacts.

Further embodiments and advantages of the system according to the present invention are evident analogously from the description of the sample transfer device according to the present invention.

Further advantages and embodiments of the invention are evident from the description of the appended drawings.

It is understood that the features recited above and those yet to be explained below are usable not only in the respective combination indicated but also in other combinations or in isolation, without departing from the scope of the present invention.

The invention is depicted schematically in the drawings on the basis of an exemplifying embodiment, and will be described below with reference to the drawings.

DETAILED DESCRIPTION OF THE INVENTION

Figure 1:
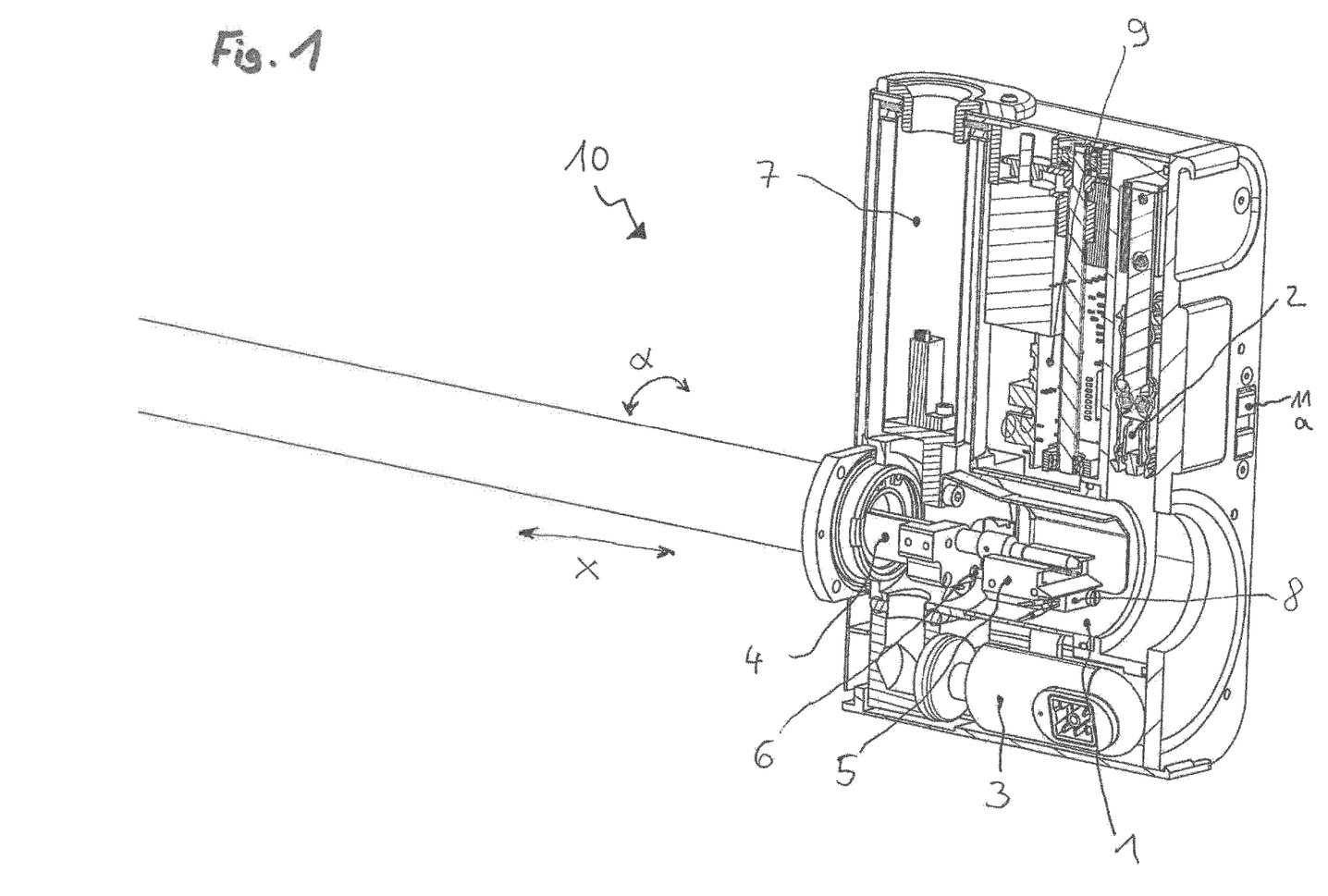
FIG. 1 is a schematic cross section through an embodiment of a sample transfer device according to the present invention.

FIG. 1 is a schematic cross section through a sample transfer device 10. A slide valve 2, with which a (vacuum)

chamber 1 can be closed off, is arranged in a housing of sample transfer device 10. Flange-mounted onto that chamber is a pressure measurement probe 3 constituting a pressure measurement device. This probe 3, in the activated state, measures the pressure (p) in chamber 1. Located in chamber 1 is a sample stage 5 that can be detachably mechanically connected to a sample holder for a sample. By means of a transfer rod 4, a sample (not depicted) mounted on the sample holder can be linearly (x) displaced, i.e. can be conveyed into a processing unit or analytical unit when slide valve 2 is open. For transfer, for example, from a processing unit into an analytical unit, the sample is brought into the interior of chamber 1 by a corresponding motion of transfer rod 4, and transferred from the processing unit to the analytical unit at a defined temperature and a defined pressure. Transfer rod 4 is rotatable ($\alpha$) around its axis. Sample stage 5 is connected via a connecting element 6 to a reservoir vessel 7. A coolant, typically liquid nitrogen, is present in reservoir vessel 7. A temperature sensor 8 is present as a second measurement device on sample stage 5. Said sensor, in the activated state, measures the temperature of sample stage 5 and thus of the sample holder connected thereto, including the sample. The measured values of pressure measurement device 3 and of temperature measurement device 8 are directed to an electronic control system 9. Alternatively or additionally, the corresponding measurement leads of the measurement devices can also be guided outward through corresponding vacuum-tight connectors in the housing of the sample transfer device, in order to be further processed by an electronic control system located, for example, on the housing of the sample transfer device.

Figure 2:
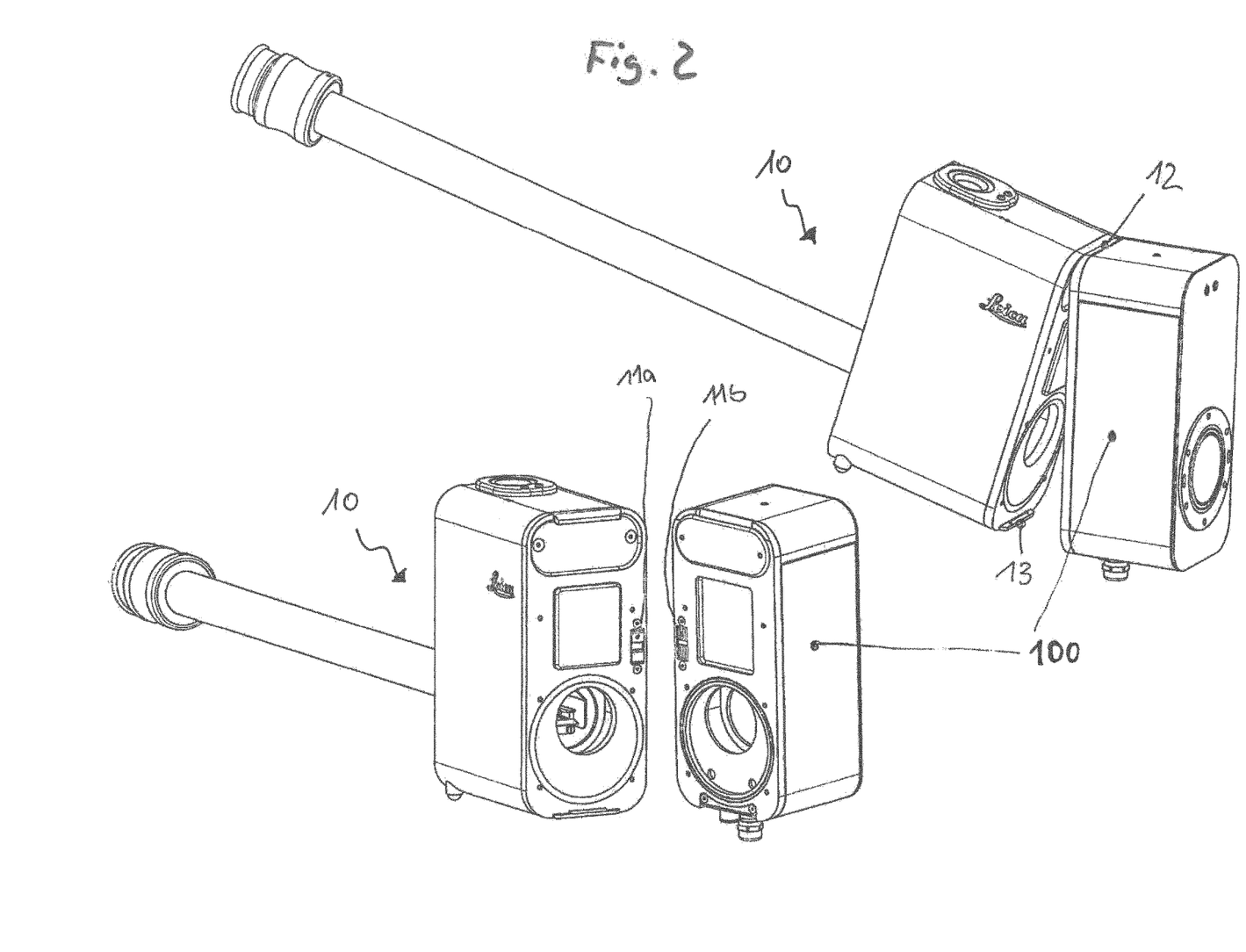
FIG. 2 is a schematic perspective view of the sample transfer device of FIG. 1 and of a suitable docking station, in two different views (FIGS. 2A and 2B)

Sample transfer device 10 possesses an attachment system (end face of the housing) to a docking station 100 (see FIG. 2). The attachment system possesses an interface having an electrical contact 11a. The attachment system furthermore possesses an opening through which a transfer of the sample out of chamber 1 into the corresponding processing unit or analytical unit can occur.

FIG. 2 shows sample transfer device 10 and a docking station 100, which as a rule is fixedly connected to the relevant processing device or analytical device. In this exemplifying embodiment, data transfer of the measured values of pressure measurement device 3 and of temperature measurement device 8, and electrical supply to the sample transfer device, are accomplished via the aforesaid interface, which comprises a resilient electrical contact 11a on the sample transfer device side. A matching contact 11b is present on docking station 100. Sample transfer device 10 is connected in vacuum-tight fashion to docking station 100 via a mechanical positioning system (stop) 12 and an interlock 13. In this state, spring contacts 11a and 11b are positioned in accurately fitted fashion with respect to one another. By way of the interface thereby produced (for example, including an RS-232 interface), electricity is supplied and the measurement devices in the sample transfer device are thus activated (in the present example, the sample transfer device does not have its own electricity supply). Temperature and pressure from the closed vacuum chamber 1 are continuously measured as physical variables, and transferred via the interface to one or more further devices as explained below. Electronic control system 9 can possess a time measurement device that is activated upon undocking and stopped upon re-docking. The transfer duration can thereby be measured. Further measured variables, for example the location and orientation of sample stage 5 or of transfer rod 4, and the position of slide valve 2, can additionally be sensed using sensors. Docking usually occurs with slide valve 2 closed, and with a slide valve (not depicted) in docking station 100 correspondingly closed. The resulting cavity is evacuated in the manner of an air lock. The slide valves are then opened, and transfer of the sample can be initiated.

Figure 3:
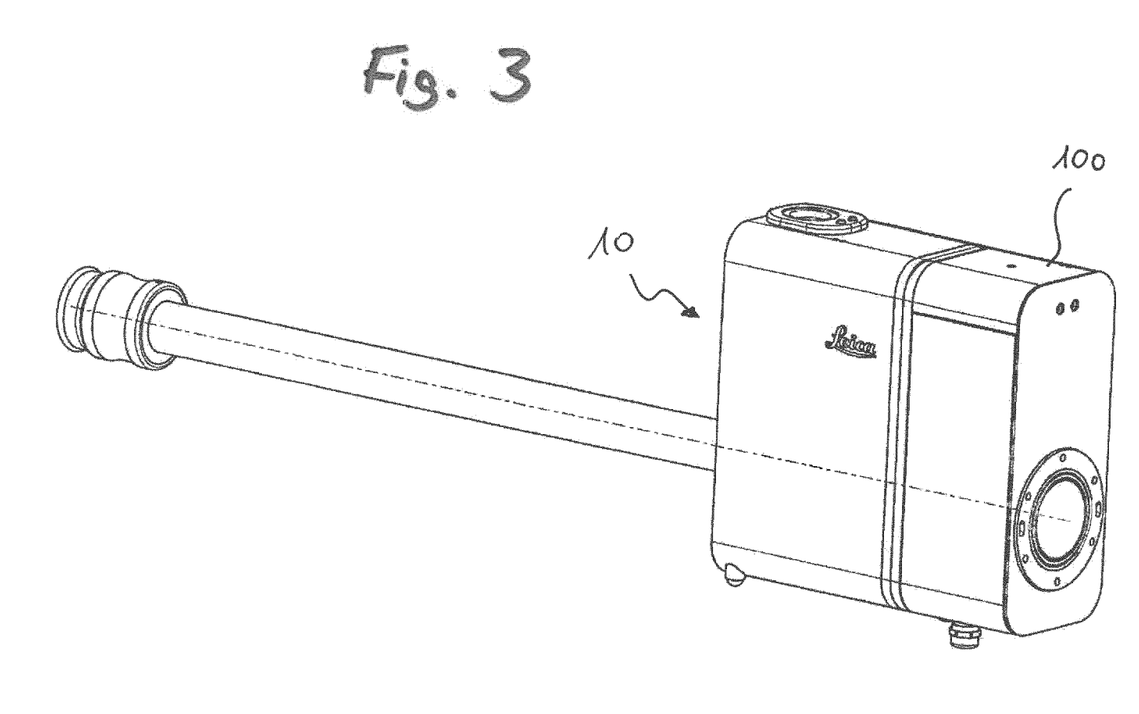
FIG. 3 shows the sample transfer device and the docking station of FIG. 2 after docking.

FIG. 3 shows sample transfer device 10 in the docked state, i.e. mechanically and electrically connected to docking station 100 (and to the subsequent processing unit or analytical unit).

Figure 4:
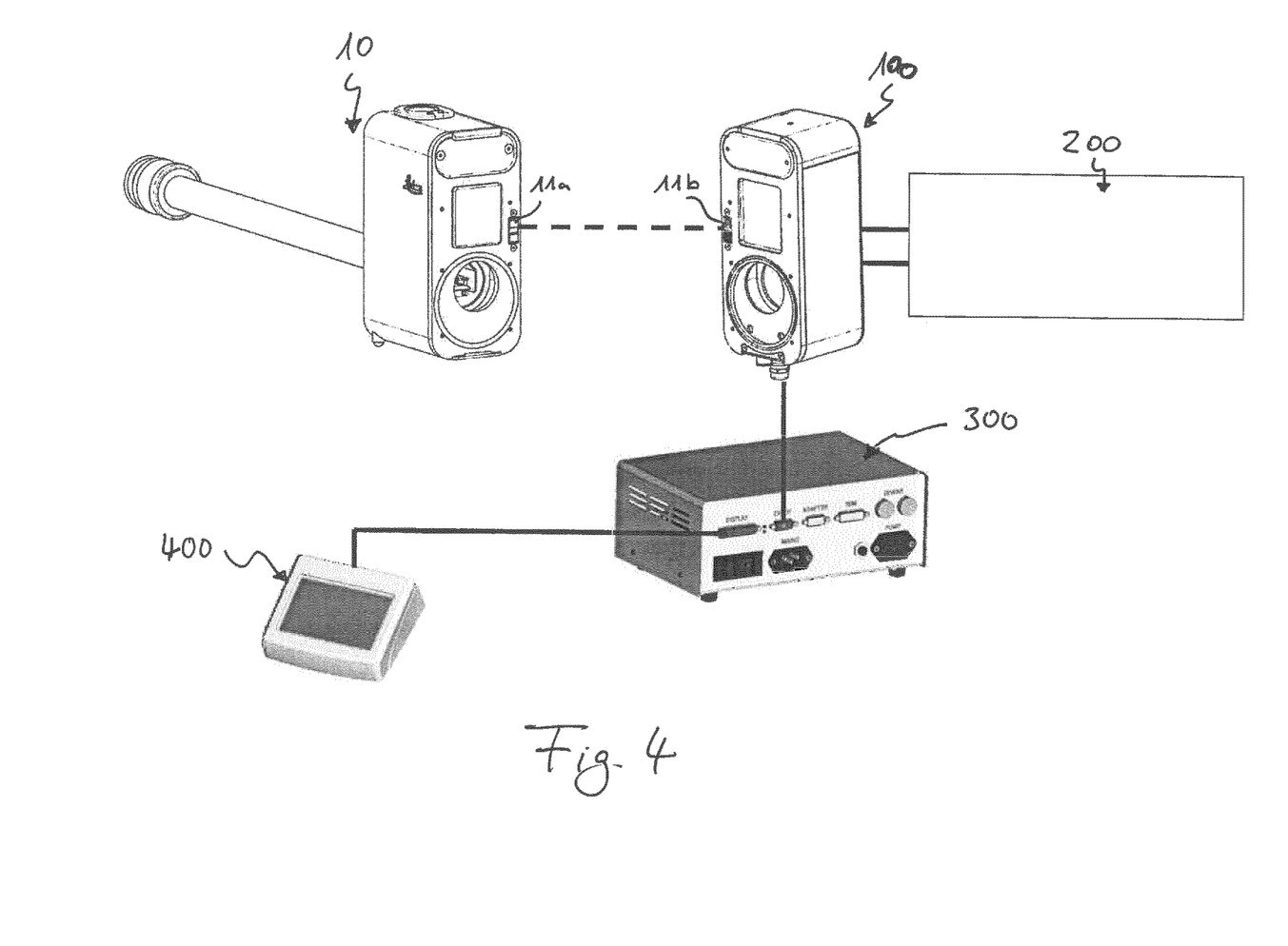
FIG. 4 shows a possible operative connection among a sample transfer device, docking station, a processing device, a control unit, and a display.

FIG. 4 shows the corresponding operative connection by way of which measured data of the measurement devices in the interior of sample transfer device 10 can be passed on to external devices. This is accomplished via the previously mentioned interface by way of which measured data can be conveyed to docking station 100 and from there to an attached processing device 200 and/or via a control unit 300 to a display 400, for example a TFT screen. If the measured data of the corresponding measurement devices are outside permitted limits, this can be correspondingly indicated and evaluated as an indication of a sample-damaging change of state. Subsequent processing or analysis of the sample can then be omitted.

In the exemplifying embodiment depicted here, the measured data, especially for the pressure and the sample temperature, are acquired upon sample transfer, i.e. in the respectively docked state. In the decoupled state, i.e. during a transfer, the supply of electricity to the sample transfer device is interrupted, and electronic control system 9 as well as measurement devices 3 and 8 are thus deactivated. Electronic control system 9 and measurement devices 3 and 8 are activated after re-docking to the subsequent processing unit or analytical unit 200 has occurred (see FIG. 4), and before sample transfer. The current measured data, especially pressure and sample temperature, are acquired. Measured values absent during the transfer can easily be interpolated by the electronic control system. If continuous acquisition, or acquisition occurring over specific time intervals, of measured values during a transfer is necessary or useful, a supply of electricity to electronic control system 9 and to measurement devices 3 and 8 is necessary; this can be effected in simple fashion via a rechargeable battery that can respectively be charged in particular in the docked state.

The elements depicted in FIG. 4—sample transfer device 10, docking station 100, processing unit 200, control unit 300, and display 400—can also be configured differently. For example, control unit 300 can be integrated into processing unit 200. Similarly, display 400 can be integrated into control unit 300 and/or into processing unit 200. With regard to sample transfer device 10, be it noted once again that electronic control system 9 explained in connection with FIG. 1 can also be arranged externally on the housing of sample transfer device 10; the same applies to any rechargeable battery that may be present and/or to any separate display that may be present. In this case the external control unit 300 and display 400 could be replaced by the electronic control system that is present on the housing of sample transfer device 10 and has a correspondingly embodied display, which usefully is likewise arranged on the housing of sample transfer device 10. With an embodiment of this kind the state of a sample in sample transfer device 10 could be continuously and autonomously monitored, independently of docking onto a docking station 100, by corresponding measurement, processing of the measured values, and display thereof.

LIST OF REFERENCE CHARACTERS

1 Chamber
2 Slide valve

3 Pressure measurement device
4 Transfer rod
5 Sample stage
6 Connecting element
7 Reservoir vessel
8 Temperature measurement device
9 Electronic control system
10 Sample transfer device
11a Contact
11b Contact
12 Mechanical positioning system, stop
100 Docking station
200 Processing unit
300 Control unit
400 Display

What is claimed is:

1. A sample transfer device (10) for reception of a sample, the sample transfer device (10) having a transfer rod (4) that is configured for reception of a sample holder, the sample holder to be arranged in a chamber (1) of the sample transfer device (10) for the purpose of transferring the sample to a processing unit or analytical unit (200),
wherein at least one measurement device (3, 8) for measuring a physical variable is arranged inside the sample transfer device (10);
wherein the at least one measurement device comprises a measurement device (8) for measuring a temperature existing in the chamber (1); and
wherein the sample transfer device (10) has a sample stage (5) that is configured for reception of the sample holder, wherein the measurement device (8) for measuring the temperature is arranged on the sample stage (5).

2. The sample transfer device according to claim 1, wherein the at least one measurement device comprises a measurement device (3) for measuring a pressure existing in the chamber (1).

3. The sample transfer device according to claim 1, wherein the at least one measurement device comprises a time measurement device.

4. A sample transfer device (10) for reception of a sample, the sample transfer device (10) having a transfer rod (4) that is configured for reception of a sample holder, the sample holder to be arranged in a chamber (1) of the sample transfer device (10) for the purpose of transferring the sample to a processing unit or analytical unit (200),
wherein at least one measurement device (3, 8) for measuring a physical variable is arranged inside the sample transfer device (10); and
wherein a rechargeable battery is arranged inside or outside the sample transfer device (10) in order to supply electricity to the at least one measurement device (3, 8).

5. The sample transfer device according to claim 1, wherein an electronic control system (9) is present which is operatively connected to the at least one measurement device (3, 8) in such a way that a measurement can be initiated by the relevant measurement device (3, 8) and/or measured values of the relevant measurement device (3, 8) can be received by the electronic control system (9).

6. The sample transfer device according to claim 1, wherein the electronic control system (9) is arranged inside the sample transfer device (10).

7. The sample transfer device according to claim 1, wherein the sample transfer device (10) comprises an interface to a docking station (100) of a processing unit or analytical unit (200).

8. A sample transfer device (10) for reception of a sample, the sample transfer device (10) having a transfer rod (4) that is configured for reception of a sample holder, the sample holder to be arranged in a chamber (1) of the sample transfer device (10) for the purpose of transferring the sample to a processing unit or analytical unit (200),
wherein at least one measurement device (3, 8) for measuring a physical variable is arranged inside the sample transfer device (10);
wherein the sample transfer device (10) comprises an interface to a docking station (100) of a processing unit or analytical unit (200); and
wherein the interface is configured in such a way that measured values of the at least one measurement device (3, 8) can be transferred to the processing unit or analytical unit (200) and/or to the associated docking station (100).

9. A sample transfer device (10) for reception of a sample, the sample transfer device (10) having a transfer rod (4) that is configured for reception of a sample holder, the sample holder to be arranged in a chamber (1) of the sample transfer device (10) for the purpose of transferring the sample to a processing unit or analytical unit (200),
wherein at least one measurement device (3, 8) for measuring a physical variable is arranged inside the sample transfer device (10);
wherein the sample transfer device (10) comprises an interface to a docking station (100) of a processing unit or analytical unit (200); and
wherein the interface is configured in such a way that the at least one measurement device (3, 8) can be supplied with electricity via the interface.

10. A sample transfer device (10) for reception of a sample, the sample transfer device (10) having a transfer rod (4) that is configured for reception of a sample holder, the sample holder to be arranged in a chamber (1) of the sample transfer device (10) for the purpose of transferring the sample to a processing unit or analytical unit (200),
wherein at least one measurement device (3, 8) for measuring a physical variable is arranged inside the sample transfer device (10);
wherein the sample transfer device (10) comprises an interface to a docking station (100) of a processing unit or analytical unit (200); and
wherein a rechargeable battery is arranged inside or outside the sample transfer device (10) in order to supply electricity to the at least one measurement device (3, 8), and wherein the interface is configured in such a way that the rechargeable battery can be charged by means of an external electricity source via the interface.

11. The sample transfer device according to claim 1, wherein the transfer rod (4) is operable for modifying the location and/or orientation of a sample holder mounted on the transfer rod (4).

12. The sample transfer device according to claim 11, wherein a further measurement device is present for detecting the location and/or orientation of the sample holder and/or a corresponding motion of the transfer rod (4).

13. A sample transfer device (10) for reception of a sample, the sample transfer device (10) having a transfer rod (4) that is configured for reception of a sample holder, the sample holder to be arranged in a chamber (1) of the sample transfer device (10) for the purpose of transferring the sample to a processing unit or analytical unit (200), wherein at least one measurement device (3, 8) for measuring a physical variable is arranged inside the sample transfer device (10);

wherein an electronic control system (9) is present which is operatively connected to the at least one measurement device (3, 8) in such a way that a measurement can be initiated by the relevant measurement device (3, 8) and/or measured values of the relevant measurement device (3, 8) can be received by the electronic control system (9); and wherein the electronic control system (9) generates a warning signal if a measured value of the at least one measurement device (3, 8) exceeds or falls below a predetermined limit value.

14. The sample transfer device according to claim 13, wherein the electronic control system (9) is arranged inside the sample transfer device (10).

15. A system comprising:

a sample transfer device (10) for reception of a sample, the sample transfer device (10) having a transfer rod (4) that is configured for reception of a sample holder, the sample holder to be arranged in a chamber (1) of the sample transfer device (10) for the purpose of transferring the sample to a processing unit or analytical unit (200), wherein at least one measurement device (3, 8) for measuring a physical variable is arranged inside the sample transfer device (10);

wherein the sample transfer device (10) comprises an interface to a docking station (100) of a processing unit or analytical unit (200); and a docking station (100) for a processing unit or analytical unit (200);

wherein the interface of the sample transfer device (10) includes a contact (11*a*) and the docking station (100) possesses a corresponding contact (11*b*), those contacts (11*a*, 11*b*) being arranged and configured in such a way that upon a connection of the sample transfer device (10) and the docking station (100), the contacts (11*a*, 11*b*) enter into an operative connection with one another.

16. The system according to claim 15, wherein the operative connection is configured in such a way that after a connection of the sample transfer device (10) and the docking station (100), measured values of the at least one measurement device (3, 8) of the sample transfer device (10) are transferred to the docking station (100) and/or to the associated processing unit or analytical unit (200), and/or the at least one measurement device (3, 8) is supplied with electricity, by way of the contacts (11*a*, 11*b*) of the sample transfer device (10) and of the docking station (100).

17. The system according to claim 15, wherein the sample transfer device (10) includes an electronic control system (9) operatively connected to the at least one measurement device (3, 8) in such a way that a measurement can be initiated by the relevant measurement device (3, 8) and/or measured values of the relevant measurement device (3, 8) can be received by the electronic control system (9), wherein the operative connection is configured in such a way that after a connection of the sample transfer device (10) and the docking station (100), the electronic control system (9) is supplied with electricity by way of the contacts (11*a*, 11*b*) of the sample transfer device (10) and of the docking station (100).

18. A sample transfer device (10) for reception of a sample, the sample transfer device (10) having a transfer rod (4) that is configured for reception of a sample holder, the sample holder to be arranged in a chamber (1) of the sample transfer device (10) for the purpose of transferring the sample to a processing unit or analytical unit (200), wherein at least one measurement device (3, 8) for measuring a physical variable is arranged inside the sample transfer device (10);

wherein the sample transfer device (10) comprises an interface to a docking station (100) of a processing unit or analytical unit (200); and wherein an electronic control system (9) is present which is operatively connected to the at least one measurement device (3, 8) in such a way that a measurement can be initiated by the relevant measurement device (3, 8) and/or measured values of the relevant measurement device (3, 8) can be received by the electronic control system (9), and wherein the interface is configured in such a way that the electronic control system (9) can be supplied with electricity via the interface.

\* \* \* \* \*